United States Patent
Attanapola et al.

(10) Patent No.: US 10,546,102 B2
(45) Date of Patent: Jan. 28, 2020

(54) PREDICTIVE ANALYTICS WORK LISTS FOR HEALTHCARE

(71) Applicant: International Business Machines Corporation, Armonk, NY (US)

(72) Inventors: Kasun L. Attanapola, Brampton (CA); Katherine D. ChengLi, Ottawa (CA); Perry R. Giffen, Kemptville (CA); Sukhwinder Lall, Ottawa (CA); Mihaela Rotaru, Ottawa (CA); Leila Sadat Rezai, Waterloo (CA)

(73) Assignee: International Business Machines Corporation, Armonk, NY (US)

( * ) Notice: Subject to any disclaimer, the term of this patent is extended or adjusted under 35 U.S.C. 154(b) by 545 days.

(21) Appl. No.: 14/997,675

(22) Filed: Jan. 18, 2016

(65) Prior Publication Data

US 2017/0206319 A1    Jul. 20, 2017

(51) Int. Cl.
*G06F 19/00*    (2018.01)

(52) U.S. Cl.
CPC .................. *G06F 19/3481* (2013.01)

(58) Field of Classification Search
CPC ........ G16H 50/30; G16H 50/20; G16H 10/60; G16H 50/70; G16H 50/50; G16H 15/00; G16H 40/20; G16H 10/20; G16H 20/10; G16H 80/00; G16H 20/30; G16H 20/60; G16H 40/63; G16H 40/67; G16H 10/40; G16H 10/65; G16H 20/00; G16H 20/13; G16H 20/70; G16H 30/40; G16H 40/40; G16H 40/60; G16H 70/20; G16H 70/40; A61K 2300/00; A61K 39/3955; A61K 2039/505; A61K 31/397; A61K 31/40;
(Continued)

(56) References Cited

U.S. PATENT DOCUMENTS 8,694,334 B2    4/2014 Ryan et al.
2010/0204920 A1 *    8/2010 Dranitsaris ............. G06F 19/00
                                                                    702/19
(Continued)

FOREIGN PATENT DOCUMENTS

WO    WO 2014/042942 A1    3/2014

OTHER PUBLICATIONS

Miyazaki, Masashi, "A Brief History of Data Analysis" Mar. 11, 2015 FlyData.*

*Primary Examiner* — Neal Sereboff
(74) *Attorney, Agent, or Firm* — Stephen R. Tkacs; Stephen J. Walder, Jr.; Ryan G. Lewis

(57) ABSTRACT

A mechanism is provided in a data processing system for generating healthcare work item recommendations based on predictive analytics. An analytics engine executing on the data processing system performs analytics to discover patterns in patient records data and to generate one or more risk scores using one or more predictive models. Each of the one or more risk scores represents a probability of a respective healthcare consideration. Each of the one or more risk scores has an associated set of contributing factors. A decision system executing on the data processing system generates a healthcare recommendation for a given patient having a given risk score based on the given risk score, a predictive model used to generate the given risk score, and a given set of contributing factors associated with the given risk score.

11 Claims, 2 Drawing Sheets

(58) Field of Classification Search
CPC ............ A61K 2039/545; A61K 31/198; A61K 31/22; A61K 31/4468; A61K 31/573; A61K 31/675; A61K 31/69; A61K 31/704; A61K 31/7048; A61K 33/24; A61K 38/05; A61K 38/07; A61K 2039/507; A61K 31/00; A61K 31/37; A61K 31/505; A61K 31/5377; A61K 39/395; A61K 45/06; A61K 9/0019; A61K 2039/54; A61K 31/455; A61K 35/413; A61K 38/179; A61K 38/45; A61K 39/00; A61K 9/0048; A61K 9/0053

See application file for complete search history.

(56) References Cited

U.S. PATENT DOCUMENTS

| | | | |
|---|---|---|---|
| 2011/0137131 A1* | 6/2011 | Adourian | G01N 33/6893 600/300 |
| 2012/0010867 A1* | 1/2012 | Eder | G06N 5/022 703/13 |
| 2012/0047105 A1* | 2/2012 | Saigal | G06N 5/048 706/52 |
| 2014/0207492 A1 | 7/2014 | Farooq et al. | |

\* cited by examiner

PREDICTIVE ANALYTICS WORK LISTS FOR HEALTHCARE

BACKGROUND

The present application relates generally to an improved data processing apparatus and method and more specifically to mechanisms for generating healthcare work item recommendations based on predictive analytics.

Analytics is the discovery and communication of meaningful patterns in data. Especially valuable in areas rich with recorded information, analytics relies on the simultaneous application of statistics, computer programming, and operations research to quantify performance. Analytics often favors data visualization to communicate insight. Systems may apply analytics to patient record data to describe, predict, and improve health recommendations for patients. Since analytics can require extensive computation, the algorithms and software used for analytics harness the most current methods in computer science, statistics, and mathematics.

SUMMARY

In one illustrative embodiment, a method, in a data processing system, is provided for generating healthcare work item recommendations based on predictive analytics. The method comprises performing, by an analytics engine executing on the data processing system, analytics to discover patterns in patient records data and to generate one or more risk scores using one or more predictive models. Each of the one or more risk scores represents a probability of a respective healthcare consideration. Each of the one or more risk scores has an associated set of contributing factors. The method further comprises generating, by a decision system executing on the data processing system, a healthcare recommendation for a given patient having a given risk score based on the given risk score, a predictive model used to generate the given risk score, and a given set of contributing factors associated with the given risk score.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
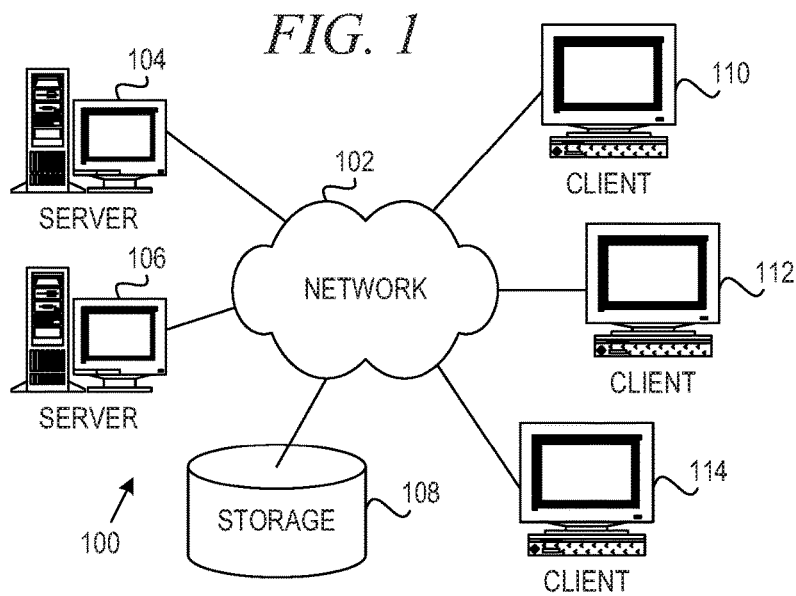
FIG. 1 is an example diagram of a distributed data processing system in which aspects of the illustrative embodiments may be implemented.

With a system for making health care recommendations for patients, it is imperative that the system organizes how work items are distributed among healthcare providers and orders the work items accordingly. With the rise of big data and analytics, predictive models may predict the risk of disease recurrence or hospital readmission. These predictive models would then be capable of outputting risk lists. Although predictive models are useful, if the results are all aggregated in one place, the different healthcare providers easily can be overwhelmed with the amount of information and the number of tasks in the work lists.

The illustrative embodiments provide a mechanism for generating work item recommendations using predictive models and taking into account contributing factors of risk scores provided by the predictive models. The mechanism categorizes and distributes work items to the appropriate healthcare providers based on a predicted risk score, the predictive model used to generate the risk score, and the factors contributing to the predicted risk score.

Before beginning the discussion of the various aspects of the illustrative embodiments, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a," "at least one of," and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

Figure 2:
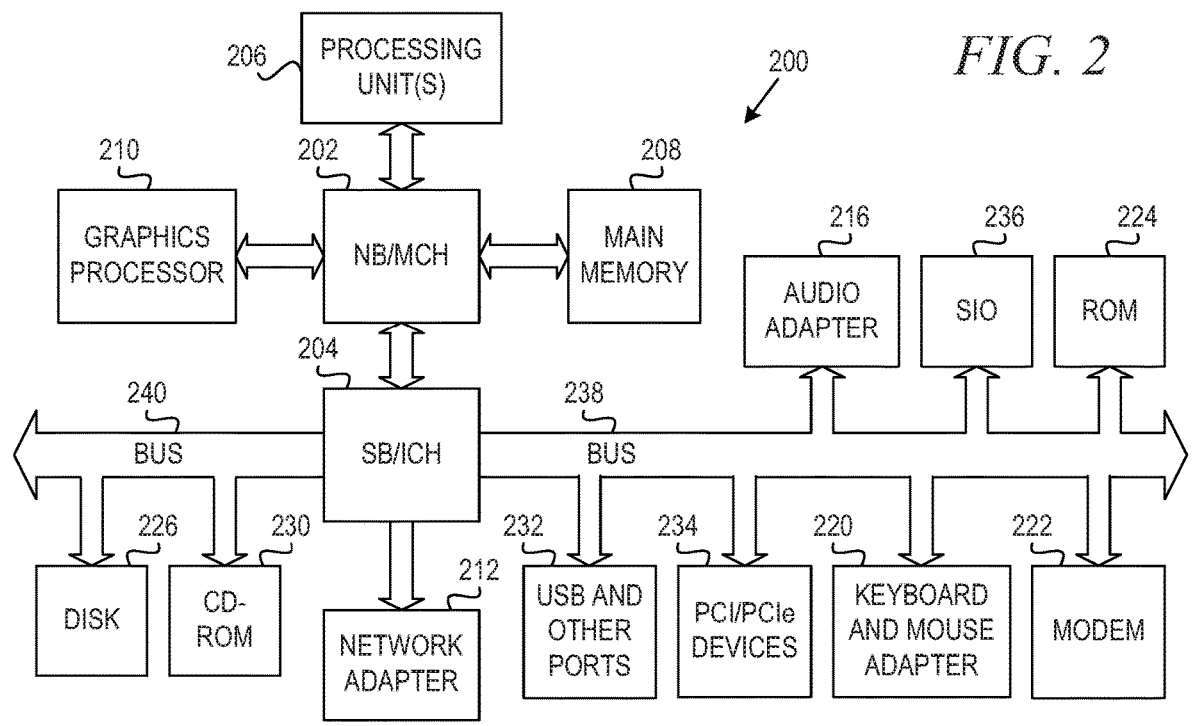
FIG. 2 is an example block diagram of a computing device in which aspects of the illustrative embodiments may be implemented.

The illustrative embodiments may be utilized in many different types of data processing environments. In order to provide a context for the description of the specific elements and functionality of the illustrative embodiments, FIGS. 1 and 2 are provided hereafter as example environments in which aspects of the illustrative embodiments may be implemented. It should be appreciated that FIGS. 1 and 2 are only examples and are not intended to assert or imply any limitation with regard to the environments in which aspects or embodiments of the present invention may be implemented. Many modifications to the depicted environments may be made without departing from the spirit and scope of the present invention.

FIG. 1 depicts a pictorial representation of an example distributed data processing system in which aspects of the illustrative embodiments may be implemented. Distributed data processing system 100 may include a network of computers in which aspects of the illustrative embodiments may be implemented. The distributed data processing system 100 contains at least one network 102, which is the medium used to provide communication links between various devices and computers connected together within distributed data processing system 100. The network 102 may include connections, such as wire, wireless communication links, or fiber optic cables.

In the depicted example, server 104 and server 106 are connected to network 102 along with storage unit 108. In addition, clients 110, 112, and 114 are also connected to network 102. These clients 110, 112, and 114 may be, for example, personal computers, network computers, or the like. In the depicted example, server 104 provides data, such as boot files, operating system images, and applications to the clients 110, 112, and 114. Clients 110, 112, and 114 are clients to server 104 in the depicted example. Distributed data processing system 100 may include additional servers, clients, and other devices not shown.

In the depicted example, distributed data processing system 100 is the Internet with network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, the distributed data processing system 100 may also be implemented to include a number of different types of networks, such as for example, an intranet, a local area network (LAN), a wide area network (WAN), or the like. As stated above, FIG. 1 is intended as an example, not as an architectural limitation for different embodiments of the present invention, and therefore, the particular elements shown in FIG. 1 should not be considered limiting with regard to the environments in which the illustrative embodiments of the present invention may be implemented.

As shown in FIG. 1, one or more of the computing devices, e.g., server 104, may be specifically configured to implement a mechanism for generating work item recommendations using predictive models and taking into account contributing factors of risk scores provided by the predictive models. The configuring of the computing device may comprise the providing of application specific hardware, firmware, or the like to facilitate the performance of the operations and generation of the outputs described herein with regard to the illustrative embodiments. The configuring of the computing device may also, or alternatively, comprise the providing of software applications stored in one or more storage devices and loaded into memory of a computing device, such as server 104, for causing one or more hardware processors of the computing device to execute the software applications that configure the processors to perform the operations and generate the outputs described herein with regard to the illustrative embodiments. Moreover, any combination of application specific hardware, firmware, software applications executed on hardware, or the like, may be used without departing from the spirit and scope of the illustrative embodiments.

It should be appreciated that once the computing device is configured in one of these ways, the computing device becomes a specialized computing device specifically configured to implement the mechanisms of the illustrative embodiments and is not a general purpose computing device. Moreover, as described hereafter, the implementation of the mechanisms of the illustrative embodiments improves the functionality of the computing device and provides a useful and concrete result that facilitates a mechanism for generating work item recommendations using predictive models and taking into account contributing factors of risk scores provided by the predictive models.

FIG. 2 is a block diagram of an example data processing system in which aspects of the illustrative embodiments may be implemented. Data processing system 200 is an example of a computer, such as client 110 in FIG. 1, in which computer usable code or instructions implementing the processes for illustrative embodiments of the present invention may be located.

In the depicted example, data processing system 200 employs a hub architecture including north bridge and memory controller hub (NB/MCH) 202 and south bridge and input/output (I/O) controller hub (SB/ICH) 204. Processing unit 206, main memory 208, and graphics processor 210 are connected to NB/MCH 202. Graphics processor 210 may be connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 may be connected to SB/ICH 204.

An operating system runs on processing unit 206. The operating system coordinates and provides control of various components within the data processing system 200 in FIG. 2. As a client, the operating system may be a commercially available operating system such as Microsoft® Windows 7®. An object-oriented programming system, such as the Java™ programming system, may run in conjunction with the operating system and provides calls to the operating system from Java™ programs or applications executing on data processing system 200.

As a server, data processing system 200 may be, for example, an IBM eServer™ System p® computer system, Power™ processor based computer system, or the like, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and may be loaded into main memory 208 for execution by processing unit 206. The processes for illustrative embodiments of the present invention may be performed by processing unit 206 using computer usable program code, which may be located in a memory such as, for example, main memory 208, ROM 224, or in one or more peripheral devices 226 and 230, for example.

A bus system, such as bus 238 or bus 240 as shown in FIG. 2, may be comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, may include one or more devices used to transmit and receive data. A memory may be, for example, main memory 208, ROM 224, or a cache such as found in NB/MCH 202 in FIG. 2.

As mentioned above, in some illustrative embodiments the mechanisms of the illustrative embodiments may be implemented as application specific hardware, firmware, or the like, application software stored in a storage device, such as HDD 226 and loaded into memory, such as main memory 208, for executed by one or more hardware processors, such as processing unit 206, or the like. As such, the computing device shown in FIG. 2 becomes specifically configured to implement the mechanisms of the illustrative embodiments and specifically configured to perform the operations and generate the outputs described hereafter with regard to a mechanism for generating work item recommendations using predictive models and taking into account contributing factors of risk scores provided by the predictive models.

Those of ordinary skill in the art will appreciate that the hardware in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

Figure 3:
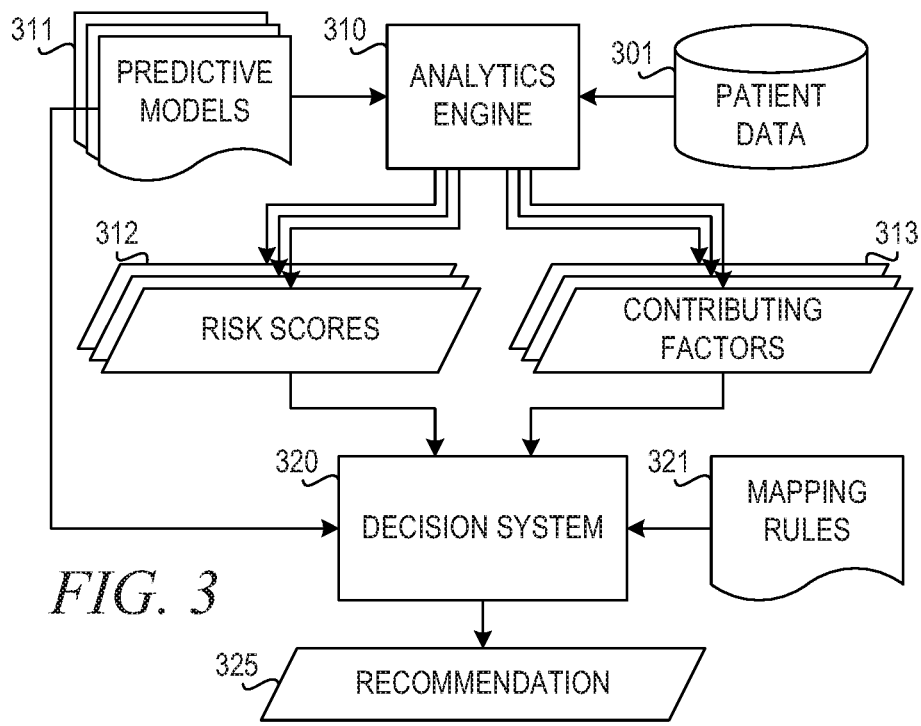
FIG. 3 is a block diagram illustrating a system for generating work item recommendations using predictive models and taking into account contributing factors of risk scores provided by the predictive models in accordance with an illustrative embodiment.

FIG. 3 is a block diagram illustrating a system for generating work item recommendations using predictive models and taking into account contributing factors of risk scores provided by the predictive models in accordance with an illustrative embodiment. Analytics engine 310 performs analytics on patient records data 301 to discover meaningful patterns in the patient records data 301. Based on these patterns, analytics engine 310 uses predictive models 311 to generate risk scores 312 and determine contributing factors 313, which are the factors in patient record data 301 that contribute significantly to risk scores 312.

Each predictive model 311 allows analytics engine 310 to discover patterns in patient record data 301 to identify patients showing a high risk of a healthcare concern, such as a given disease, disorder, syndrome, other medical condition, disease recurrence, hospital readmission, or the like. For example, a given predictive model 311 may allow analytics engine 310 to generate risk scores 312, each risk score 312 representing a probability of a healthcare consideration or concern, and to identify a patient showing an increased risk of psychological distress. Predictive models 311 predict a probability of failure or the impact of a failure.

Each risk score 312 is associated with a predictive model 311. In addition, each risk score 312 is linked to outstanding factors 313 leading to a recommendation. Based on the risk scores 312, predictive model used 311, contributing factors 313, and mapping rules 321, decision system 320 generates recommendation 325 to queue a work item to a list of particular health providers. Mapping rules 321 link a contributing factor or a combination of contributing factors 313 to specific health care providers. In on embodiment, best practices are encoded within mapping rules 321 in combination with rules for mapping risk factors with healthcare providers. Decision system 320 may also have functionality for compliance validation for best practices. In another embodiment, mapping rules 321 may also take into account availability of resources, priority information, and operational safety and efficiency of each given healthcare provider.

As an example, consider a predictive model 311 used to detect risks of heart attack. Analytics engine 310 predicts a high risk score 312 for a given patient, John. The input factors to this prediction model include the stress level of the patient, the heartbeat of the patient, the systolic and diastolic blood pressure measurements, the patient's age, and the patient's weight. The attributes (factors) for John in patient data 301 result in a high risk score 312, which triggers decision system 320 to generate recommendation 325. In this example, John has a high stress level, which is a significant contributing factor 313 for the high risk score 312. In this case, decision system 320 uses mapping rules 321 to recommend distributing a work item to a work list of a therapist to provide counseling for stress and anxiety and a work list for a general practitioner, but not to a work list of a cardiologist, depending on best practices.

As another example, consider a predictive model that predicts when a patient with chronic renal failure will be readmitted to the hospital. The input for the model includes factors such as the patient's weight, blood pressure, creatinine level, medications, and activity level. There are three people involved in the care of the patient: the nephrologist, the family doctor, and the nurse at the renal clinic. If the model shows a high risk of readmission due to weight gain, the decision system generates a work item for the renal clinic nurse to contact the patent and check for causes of weight gain. If the model shows a high risk of readmission due to lower activity level, then the decision system generates a work item for the clinic nurse to contact the patient and investigate. If the model shows a high risk of readmission due to an elevated creatinine, then the decision system generates a work item for the nephrologist to consider an earlier dialysis treatment. And if the model shows a high risk of readmission due to the patient not refilling a prescription, then the decision system generates a work item for the family doctor to contact the patient.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Figure 4:
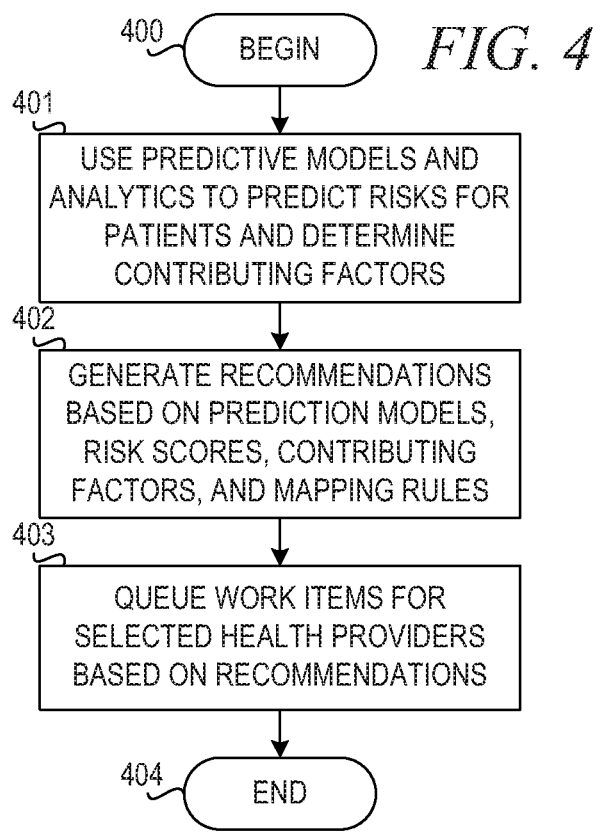
FIG. 4 is a flowchart illustrating operation of a system for generating work item recommendations using predictive models and taking into account contributing factors of risk scores provided by the predictive models in accordance with an illustrative embodiment.

FIG. 4 is a flowchart illustrating operation of a system for generating work item recommendations using predictive models and taking into account contributing factors of risk scores provided by the predictive models in accordance with an illustrative embodiment. Operation begins (block 400), and the system uses predictive models and analytics to predict risks for patients and to determine contributing factors (block 401). The system generates recommendations based on the prediction model used, the risk scores, contributing factors, and mapping rules (block 402). The system then queues work items for selected health care providers based on the recommendations and the mapping rules (block 403). Thereafter, operation ends (block 404).

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems and Ethernet cards are just a few of the currently available types of network adapters.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising a processor and a memory, wherein the memory stores instructions for configuring the processor to implement an analytics engine and a decision system for generating healthcare work item recommendations based on predictive analytics, the method comprising:

performing, by the analytics engine executing on the processor of the data processing system and configured with one or more predictive models, analytics to discover patterns in patient records data, to generate one or more risk scores using the one or more predictive models based on a set of attributes in the patient records data and the discovered patterns in the patient records data, wherein each of the one or more risk scores represents a probability of a respective healthcare consideration, and to identify for each of the one or more risk scores an associated set of contributing factors, wherein the set of contributing factors is a subset of the set of attributes that contribute to the risk score;

generating, by the decision system executing on the processor of the data processing system, a healthcare recommendation for a given patient having a given risk score based on the given risk score, a predictive model used to generate the given risk score, and a set of mapping rules that link contributing factors to healthcare providers; and queuing, by the decision system executing on the processor of the data processing system, at least one work item for at least one selected healthcare provider based on the healthcare recommendation.

2. The method of claim 1, wherein healthcare recommendation comprises a work item and a distribution of the work item to a selected healthcare provider.

3. The method of claim 1, wherein the set of mapping rules comprises rules based on availability of resources, rules based on priority information, and rules based on operational safety and efficiency of each given healthcare provider.

4. The method of claim 1, wherein the respective healthcare consideration comprises a disease, a disorder, a syndrome, a disease recurrence, or hospital readmission.

5. A computer program product comprising a non-transitory computer readable storage medium having a computer readable program stored therein, wherein the computer readable program, when executed on a data processing system, causes the implement an analytics engine and a decision system for generating healthcare work item recommendations based on predictive analytics, wherein the computer readable program causes the data processing system to:

perform, by the analytics engine executing on a processor of the data processing system and configured with one or more predictive models, analytics to discover patterns in patient records data, to generate one or more risk scores using the one or more predictive models based on a set of attributes in the patient records data and the discovered patterns in the patient records data, wherein each of the one or more risk scores represents a probability of a respective healthcare consideration, and to identify for each of the one or more risk scores an associated set of contributing factors, wherein the set of contributing factors is a subset of the set of attributes that contribute to the risk score;

generate, by the decision system executing on the processor of the data processing system, a healthcare recommendation for a given patient having a given risk score based on the given risk score, a predictive model used to generate the given risk score, and a set of mapping rules that link contributing factors to health care providers; and queue, by the decision system executing on the processor of the data processing system, at least one work items for at least one selected healthcare provider based on the healthcare recommendation.

6. The computer program product of claim 5, wherein healthcare recommendation comprises a work item and a distribution of the work item to a selected healthcare provider.

7. The computer program product of claim 5, wherein the set of mapping rules comprises rules based on availability of resources, rules based on priority information, and rules based on operational safety and efficiency of each given healthcare provider.

8. The computer program product of claim 5, wherein the respective healthcare consideration comprises a disease, a disorder, a syndrome, a disease recurrence, or hospital readmission.

9. An apparatus comprising:
a processor; and
a memory coupled to the processor, wherein the memory comprises instructions which, when executed by the processor, cause the processor to implement an analytics engine and a decision system for generating healthcare work item recommendations based on predictive analytics, wherein the instructions cause the processor to:

perform, by the analytics engine executing on the processor and configured with one or more predictive models, analytics to discover patterns in patient records data, to generate one or more risk scores using the one or more predictive models based on a set of attributes in the patient records data and the discovered patterns in the patient records data, wherein each of the one or more risk scores represents a probability of a respective healthcare consideration, and to identify for each of the one or more risk scores an associated set of contributing factors, wherein the set of contributing factors is a subset of the set of attributes that contribute to the risk score;

generate, by the decision system executing on the processor, a healthcare recommendation for a given patient having a given risk score based on the given risk score, a predictive model used to generate the given risk score, and a set of mapping rules that link contributing factors to healthcare providers; and queue, by the decision system executing on the processor of the data processing system, at least one work items for at least one selected healthcare provider based on the healthcare recommendation.

10. The apparatus of claim 9, wherein healthcare recommendation comprises a work item and a distribution of the work item to a selected healthcare provider.

11. The apparatus of claim 9, wherein the set of mapping rules comprise rules based on availability of resources, rules based on priority information, and rules based on operational safety and efficiency of each given healthcare provider.

* * * * *